United States Patent [19]

Daoud

[11] Patent Number: 5,342,180
[45] Date of Patent: Aug. 30, 1994

[54] PUMP MECHANISM HAVING A DRIVE MOTOR WITH AN EXTERNAL ROTOR

[75] Inventor: Adib G. Daoud, San Diego, Calif.

[73] Assignee: IVAC Corporation, San Diego, Calif.

[21] Appl. No.: 977,826

[22] Filed: Nov. 17, 1992

[51] Int. Cl.$^5$ .................. F04B 43/08; F04B 17/00
[52] U.S. Cl. .................... 417/412; 417/474; 310/67 R
[58] Field of Search ............ 417/474–477, 417/412; 310/67 R

[56] References Cited

U.S. PATENT DOCUMENTS

| | | | |
|---|---|---|---|
| 1,922,196 | 8/1933 | Butler | 417/474 |
| 2,682,617 | 9/1949 | Reich et al. | 310/67 |
| 3,760,207 | 9/1973 | Abraham et al. | 310/49 |
| 3,806,744 | 4/1974 | Abraham et al. | 310/49 |
| 4,143,425 | 3/1979 | Runge | 417/412 |
| 4,293,961 | 10/1981 | Runge | 417/412 |
| 4,604,034 | 8/1986 | Wheeldon et al. | 417/18 |
| 4,648,812 | 3/1987 | Kubayashi et al. | 417/477 |
| 4,653,987 | 3/1987 | Tsuji et al. | 417/412 |
| 4,672,250 | 6/1987 | Seitz | 310/90 |
| 4,686,400 | 8/1987 | Fujisaki et al. | 310/67 |
| 4,771,197 | 9/1988 | Ivanto et al. | 310/67 |
| 4,814,651 | 3/1989 | Elris | 316/67 R |
| 4,954,046 | 9/1990 | Irvin et al. | 417/474 |
| 5,211,548 | 5/1993 | Okada | 417/474 |

*Primary Examiner*—Richard A. Bertsch
*Assistant Examiner*—Peter Korytnyk
*Attorney, Agent, or Firm*—Fulwider, Patton, Lee & Utecht

[57] ABSTRACT

A pump mechanism using a drive motor having an external rotor. In one case, cams are mounted on the external surface of the rotor. Cam followers or peristaltic fingers engage the cams and move linearly in response to the rotational cam motion. The cam surfaces are rotated from adjacent cam surfaces to achieve a peristaltic effect through the peristaltic fingers sequentially pressing against the fluid tubing. In another case, the external surface of the rotor is threaded and elongated. A nut is mounted on the rotor and confined to travel in only a linear direction. A coupling arm is connected between the nut and a syringe plunger to force the plunger into the syringe barrel and thereby move the fluid.

18 Claims, 4 Drawing Sheets

FIG. 3
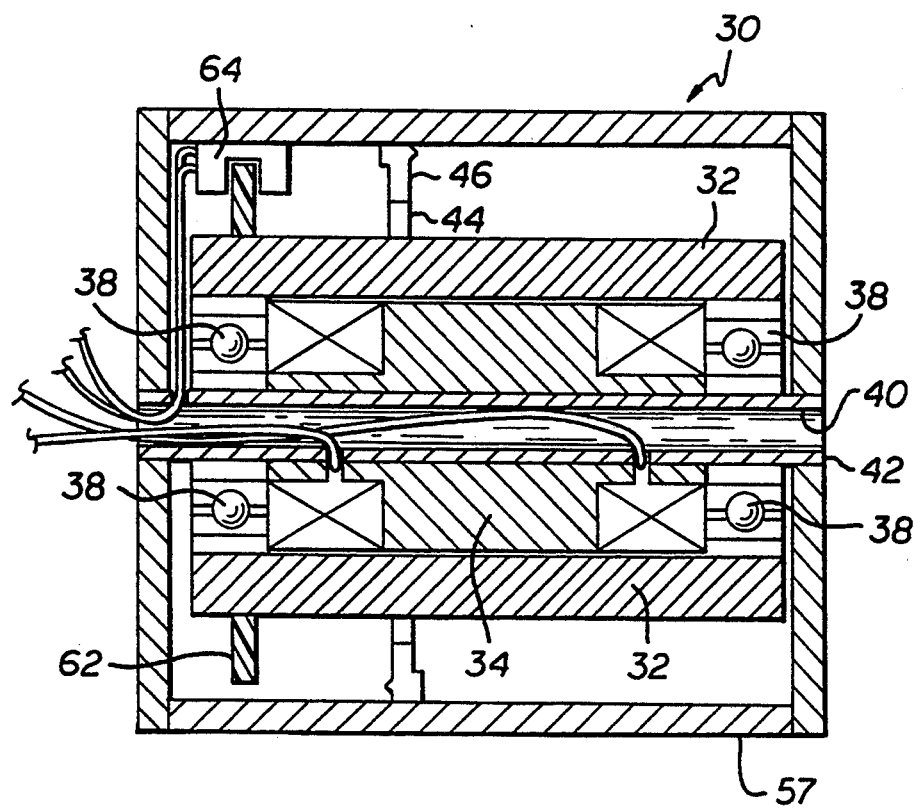
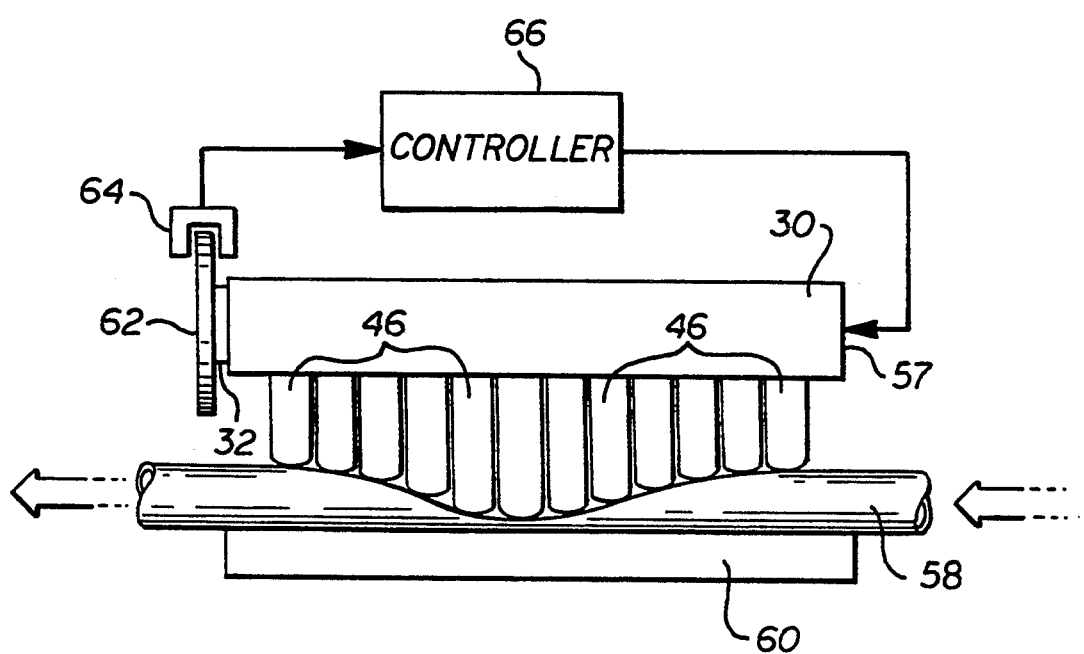
FIG. 4

FIG. 5
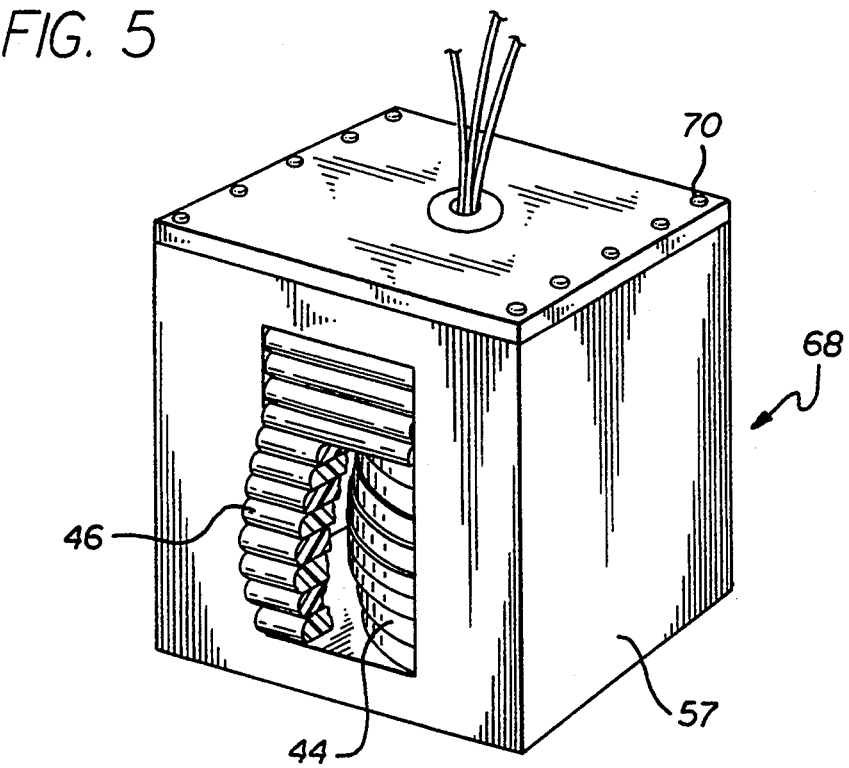
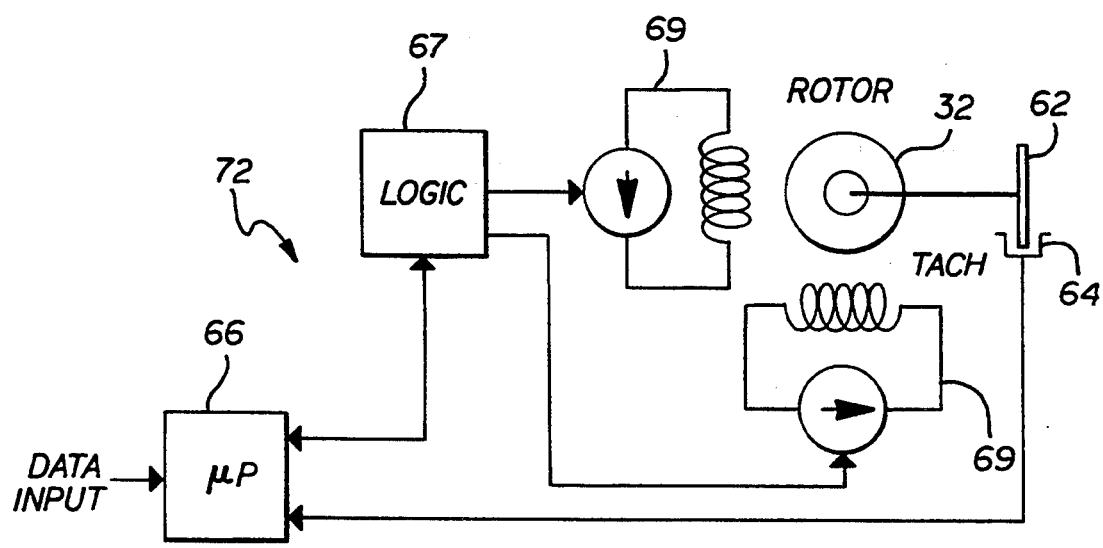
FIG. 6

PUMP MECHANISM HAVING A DRIVE MOTOR WITH AN EXTERNAL ROTOR

BACKGROUND

The invention relates generally to drive mechanisms and more particularly, to external rotor drive mechanisms used in pumping intravenous infusion fluids.

Positive pressure infusion systems include a pumping mechanism which forces the infusion fluid from a fluid supply through a fluid conduit to a patient. The fluid supply may take various forms including a collapsible bag, a bottle or a syringe. One typical type of infusion pump includes a peristaltic pumping mechanism for creating a moving zone of occlusion in the fluid conduit to move the infusion fluid through the conduit to the patient.

In typical peristaltic pumping mechanisms, a stepper or other type of motor supplies rotational drive motion which is translated to linear drive motion by means of a peristaltic drive mechanism including peristaltic fingers which themselves form the moving zone of occlusion. The output of the stepper motor is typically coupled to a cam shaft by means of a drive belt or gears. Coupled to the cam shaft is a set of cam followers or peristaltic fingers which are mounted to convert the rotational drive motion of the cams into linear drive motion. These peristaltic fingers move against the fluid line to create the moving zone of occlusion and move the fluid through the fluid line.

An example of one such mechanism is shown in FIG. 1. A pumping mechanism 10 includes a stepper motor 12 used to drive a peristaltic mechanism 14 through a drive belt 16. The peristaltic mechanism includes a plurality of peristaltic fingers 18 coupled to a respective plurality of cams 20. The output shaft 22 of the stepper motor 12 turns an attached drive gear 24 which moves the drive belt 16. A drive pulley is attached to the cam shaft 28 of the peristaltic mechanism 14 to rotate the cams 20. Each cam 20 drives a particular peristaltic finger 18. The angles between adjacent cams are selected so that the peristaltic fingers occlude the conduit in a sequential manner thus creating the peristaltic effect.

Such a mechanism as that shown in FIG. 1 can occupy a relatively large space and includes mechanical inefficiencies caused by the linkages between the drive motor and the work done by the peristaltic fingers. Some of these inefficiencies result from the typical difficulties associated with mechanical drives, such as backlash, slippage, compliance of the belt and tolerances existing in any gear drives, belt drives, and in any mechanical linkages. Additionally, such a belt or gear driven mechanism includes a larger number of parts which consequently increases the size, complexity, cost and weight of the pumping mechanism.

Another prior drive mechanism in fluid infusion systems is the rotating lead screw most often used with syringe pumps. In this arrangement, the output shaft of an electric motor is coupled to an elongated lead screw through a drive belt or gears. A nut device, such as a half-nut, is mounted on the threads of the lead screw and slides along one or more rails which confine the nut device to linear motion. As the lead screw turns, the nut device moves linearly. A pushing arm is coupled to the nut device and engages the plunger of a syringe to press the plunger into the syringe thereby forcing the syringe contents into an administration set for ultimate delivery to a patient.

Such lead screw syringe pumps also suffer from mechanical inefficiencies associated with drive gears, drive belts such as backlash, slippage, compliance of the belt and tolerances existing in any gear drives, belt drives, and in any mechanical linkages. Additionally, such a belt or gear driven mechanism between the motor and the lead screw includes a larger number of parts which consequently increases the size, complexity, cost and weight of the pumping mechanism.

A further consideration is length of battery life. Many pumps are portable and use battery power for operation. Additionally, many other pumps have a battery backup feature which comes into use in the event that the main power for the pump ceases. In both cases, the length of the battery life is an important consideration. In cases where the pump mechanism requires relatively large amounts of power due to mechanical inefficiencies, larger and heavier batteries, or an increased number of batteries are required to obtain the battery life desired. This results in increased weight, size, and expense of the pump. Additionally, recharge times may be extended thus impacting pump service. Such batteries also tend to limit the portability of a pump. Heavier pumps are not considered as portable as lighter pumps. Therefore, mechanical efficiency can greatly affect the performance of a pump from a power consideration.

Hence those concerned with drive mechanisms in fluid infusion have recognized that it would be beneficial to provide a lighter, more efficient and smaller, and less costly pumping mechanism, yet one which is accurate and relatively simple to manufacture. In addition, a more mechanically efficient pump having lessened power requirements is desirable. The present invention fulfills these needs and others.

SUMMARY OF THE INVENTION

The present invention provides apparatus and method for applying a force to a fluid containment device to cause fluid in the device to move from one position to another through the use of an electric motor comprising a stator and a rotor with the rotor being located such that it rotates about the stator. A drive device mounted on the outer surface of the rotor rotates with the rotor to provide a rotational driving force. Coupled to the rotor-mounted drive device is a follower to translate the rotational drive force of the drive device into a linear drive force. The follower has a contact surface for engaging the fluid container and causing the fluid to move in response to the linear drive force. In one aspect, the external rotor comprises a permanent magnet.

In one form, the drive device comprises a cam formed on or attached to the outer surface of the rotor and the follower comprises a cam follower positioned around the cam for moving in a linear manner in response to the rotational drive force of the cam. The cam follower has a contact surface and functions as a peristaltic finger with the contact surface pressing against the fluid container to move the fluid. Where the fluid container comprises a flexible tubing, the peristaltic finger occludes the tubing thereby moving the fluid through the tubing.

In another form, the drive device comprises a plurality of cams, each of which is mounted on the cam shaft such that the highest point of its raised cam surface is rotated at a predetermined angle from those of adjacent cams. The cam followers thus press against the tubing at different times and locations. By selecting the proper angular relationship between the camming surfaces of adjacent cams, a peristaltic mechanism is formed causing fluid to flow through an occlusion zone of the tubing.

In another form, the drive device comprises a threaded surface located on the external rotor surface. In this case, the rotor is elongated and with the threads, appears and functions as a lead screw. The follower comprises a nut device which is mounted on the threads of the rotor. The nut device is confined to travel in only a linear direction, thus converting the rotational drive force of the lead screw rotor into linear drive force. By including a coupling arm from the translating nut device to the plunger of a syringe for example, the contents of the syringe may be forced out of the syringe into an administration tubing and ultimately into a patient.

Other aspects and advantages of the invention will become apparent from the following detailed description and with accompanying drawings, illustrating by way of example the features of the invention.

BRIEF DESCRIPTION OF THE DRAWINGS

FIG. 3 is a cross-sectional view of an external rotor motor usable in the invention;

FIG. 4 is a block diagram of a multi-finger peristaltic mechanism in accordance with the invention using an external rotor motor;

FIG. 5 is an assembled perspective view of the external rotor motor used in a multi-finger peristaltic mechanism;

FIG. 6 is a basic electrical diagram for the external rotor motor mechanism of FIG. 2;

DETAILED DESCRIPTION OF THE PREFERRED EMBODIMENTS

Figure 2:
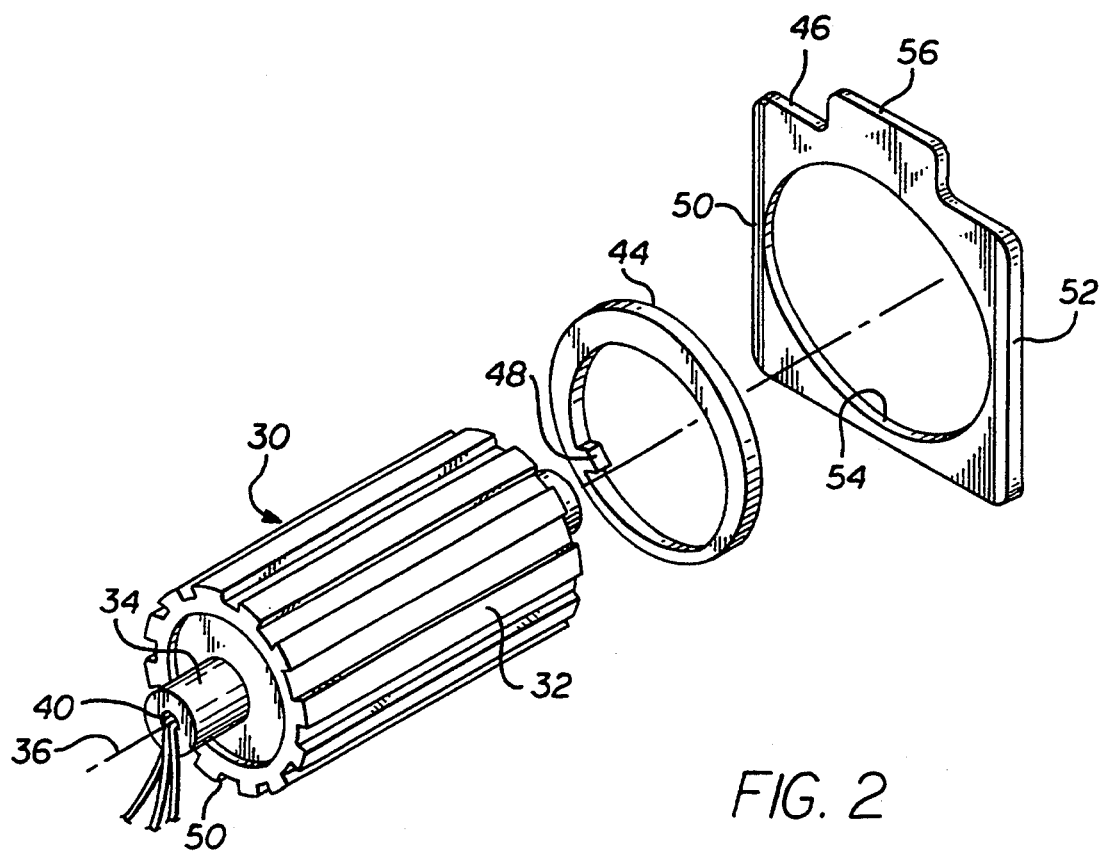
FIG. 2 is an exploded perspective view of a motor having an external rotor having keyways formed into the external surface of the rotor, a cam with a key for being located in one of the keyways, and a cam follower with a contacting surface for engagement with the fluid tubing.

Referring now to the drawings with more particularity wherein like reference numerals designate like or corresponding elements among the several views, there is shown in FIG. 2 a pump mechanism in accordance with the principles of the invention. A motor 30 is shown having an external rotor 32. The stator 34, or stationary part of the motor, is positioned along the centerline 36 of the motor 30 and the rotor 32 rotates about the stator 34 and about the centerline 36. In this case, the motor 30 is a stepper motor. A passage 40 is formed in the stator 34 and is used for the electrical lines to the motor 30.

A cross-sectional view of the motor 30 of FIG. 2 is presented in FIG. 3. As shown, the rotor 32 is mounted to the stator 34 by means of a set of bearings 38 at each end of the stator 34. Sealed ball bearings are used in this embodiment and are pressed into place to properly position the rotor 32 about the stator 34. A manufacturer from which such sealed bearings are available is Motion Industries, Inc. located in San Diego, Calif.

A center shaft 42 is firmly mounted to the stator 34 and provides the passage 40 into the interior of the motor 30 for the electrical lines. In this case, the stator 34 contains the electromagnetic circuits for establishing rotating magnetic fields. These coils are described in further detail below in relation to FIG. 6. The rotor 32 in this case comprises permanent magnets which will interact with the rotating magnetic fields created in the stator 34 to result in rotation of the rotor 32. Although not shown in the drawings, the rotor may be ridged on its inside surface to function as a stepper motor having discrete angular movements, for example 1.8° steps.

Referring again to FIG. 2, the pump mechanism of this embodiment also includes a cam 44 and a cam follower 46. The cam 42 in this embodiment further includes a key 48 which is shaped to fit into one of the keyways 50 formed on the outer surface of the rotor 32. This key/keyway arrangement provides for firm mounting of the cam 44 onto the rotor 32 so that the cam rotates precisely with the rotor. Additionally, by forming multiple keyways in the rotor 32 which are spaced apart from each other by predetermined angles, the sequential, or peristaltic effect of the followers 46 can be produced as will be described in more detail below.

The follower 46 includes two outside slide rails 50 and 52, which are used to guide the follower in its movement inside its case and to separate each follower from adjacent followers. Further discussion of this feature is provided below. The follower 46 also includes a drive aperture 54 for receiving the cam 44, and a contact surface or peristaltic finger 56 for contacting a fluid containment device, such as a fluid tubing, to cause fluid to flow through the tubing. As will be described below in more detail, the follower 46 translates the rotational drive motion of the cam 44 into linear drive motion.

Referring now to FIGS. 4 and 5, a series of twelve cam followers 46 are driven by the motor 30 having an external rotor 32. Although the numerals 46 are only shown pointing to a few followers, all followers are intended to be referred to by numeral 46. The cam followers 46 are mounted in a case 57 and are engaged with a fluid tubing 58 for moving fluid through the tubing. A pressure plate 60 continuously presses the tubing 58 into contact with the peristaltic fingers 46. A position disk 62 is coupled to the external rotor 32 of the motor 30 and rotates therewith. An optical sensor 64 provides electrical signals to the motor controller 66 indicative of the stepper motor position. The motor controller 66 provides signals to the motor 30 to speed up or slow down as are required to maintain the selected speed corresponding to the selected infusion rate. By sequencing the cams 44 (FIG. 2) properly, the peristaltic effect shown in FIG. 4 is achieved by the peristaltic fingers 46. The broad arrows indicate fluid movement through the tube 58.

Figure 1:
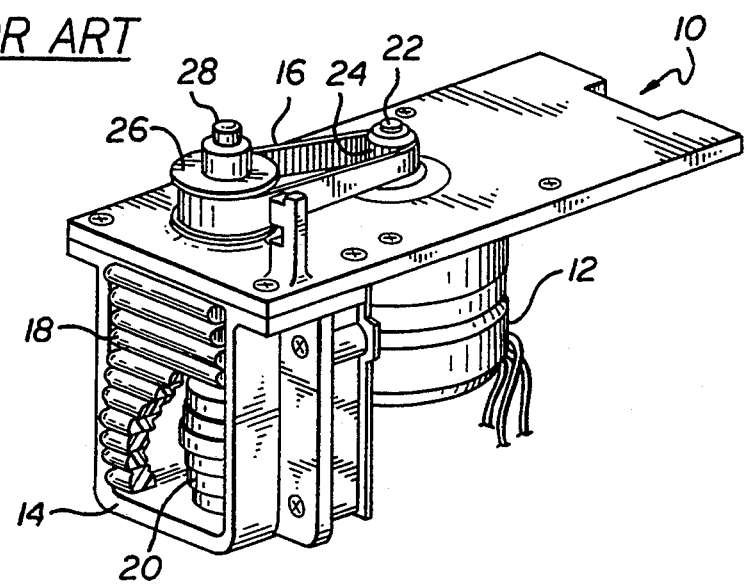
FIG. 1 is a view of a prior an pump comprising a separate motor and peristaltic mechanism for operating on a fluid conduit to move fluid to a patient.

Referring now in more detail to FIG. 5, a motor drive mechanism 68 with an external rotor in accordance with the principles of the invention is shown. In the mechanism of FIG. 5, a case 57 contains the motor, the cams 44 and the followers 46. Mounting holes 70 are provided for mounting the motor drive mechanism 68 inside an infusion pumping device. As is apparent from FIG. 5, the size of the pumping mechanism 68 is smaller than that of the pumping mechanism of FIG. 1. Additionally, there are fewer parts and no drive belt or gear couplings. Thus, the associated inefficiencies have been eliminated.

The cam followers 46 in FIG. 5 are constrained by the case 57 that allows them to only move linearly. By also referring to FIG. 3, the method of translating the rotary motion of the cams into linear motion of the cam followers 46 can be seen. The cam followers 46 are of a size and shape such that they fit inside the case 57 closely. The inside of the case 57 has flat surfaces against which the flat surfaces of the followers 46 move along. Because the cams 44 contact the inside surfaces 54 of the followers 46, they impart motion to the followers 46. However, the followers 46 have a close fit with the inside surfaces of the case 57 and can move in only a linear direction. They are not permitted to rotate along with the cams 44 because their flat surfaces contact the inside surfaces of the case 57. Thus a translation of motion from rotary to linear occurs.

Furthermore, also referring once again to FIG. 2, the cam followers 46 surround the cams 44. When the cam 44 rotates, the eccentricity of the cam and its geometric center causes the radius of contact to vary and drive the cam follower 46 in a reciprocal manner. Because the cam 44 has a solid body, the cam follower 46 can be moved by the cam 44 in a positive, reliable manner. Thus there is no need for a return spring to act on the cam follower 46 to return it to its original position after it has been displaced by the cam 44.

Referring now to FIG. 6, a very brief schematic diagram of an electrical circuit 72 for powering the stator and creating rotating magnetic fields is shown. The motor controller 66, which in this embodiment is indicated as comprising a microprocessor ($\mu P$) controls the logic circuit 67 which controls the individual windings 69 to obtain rotary motion. Electrical circuits 72 for powering motors are well known in the art and no further detail is provided here.

Figure 7:
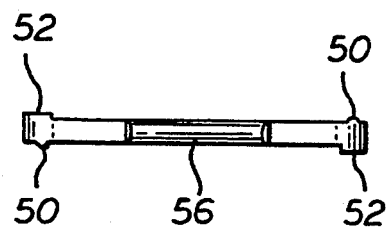
FIG. 7 is a top view of a cam follower usable in the pumping mechanism shown in FIG. 2.

Referring now to FIG. 7, a top view of a cam follower 46 in accordance with this embodiment is shown. The cam follower 46 includes two rails 50 and 52 having different shapes. The first rail 50 has a rounded surface while the second rail 52 is flat. The positioning of the first and second rails is such that the first rail 50 of one follower 46 will contact the second rail 52 of the adjacent follower. This will result in the curved surface of one rail contacting the flat surface of the adjacent rail. The use of the curved surface results in a reduced contact between adjacent followers and lower friction.

Figures 8, 9:
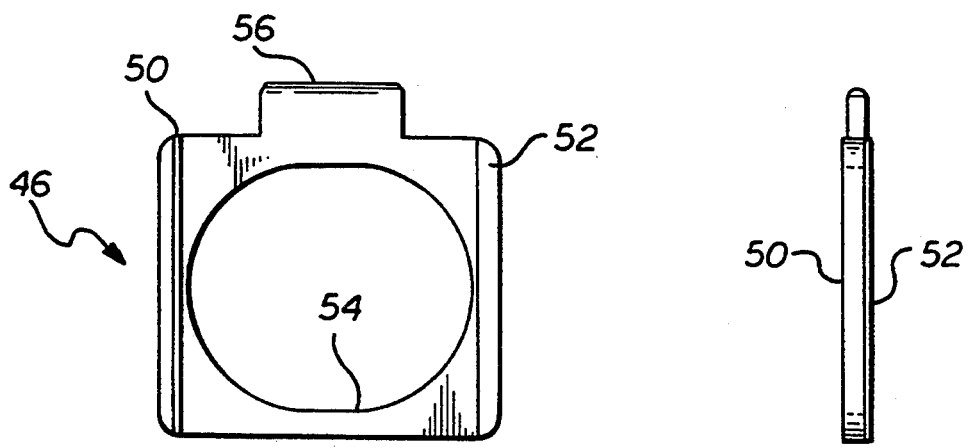
FIG. 8 is a front view of the cam follower of FIG. 7.
FIG. 9 is a side view of the cam follower of FIG. 7.

FIG. 8 is a front view of the follower 46 showing that the first and second rails 50 and 52 extend completely along the follower 46. FIG. 9 is a side view of the follower 46 showing the protrusion of the first and second rails 50 and 52.

Figure 10:
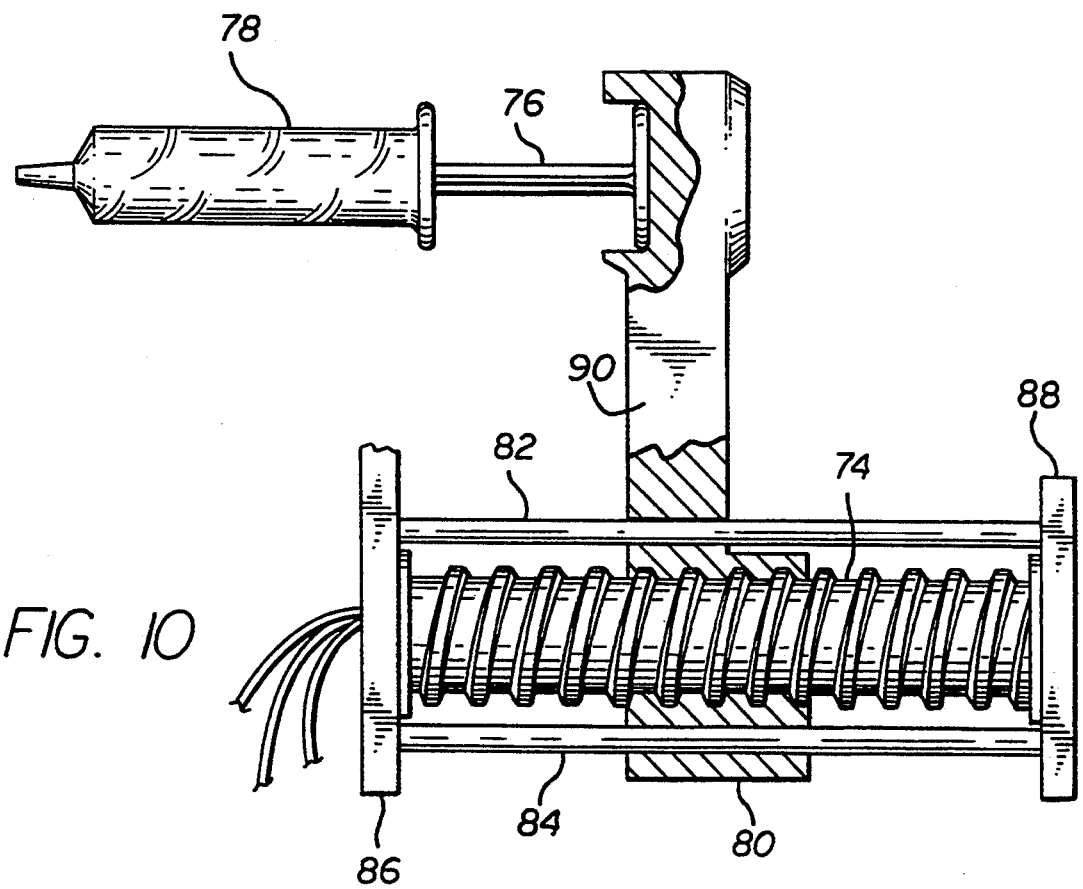
FIG. 10 is a top view of a motor having an external rotor with threads formed into the external rotor and a nut mounted on those threads for moving the plunger of a syringe in a syringe pump mechanism.

In a further embodiment in accordance with the invention, threads 74 are formed in the external surface of the rotor as shown in FIG. 10. The external rotor thus appears as a lead screw. In this case, the rotor is elongated to provide the full length needed for movement of a syringe plunger 76 completely into the syringe barrel 78. A half-nut 80 engages the threads 74 and moves along the threaded rotor 74 in accordance with rotor rotation. The half-nut also engages the rails 82 and 84 which confine the half-nut to linear motion thus translating the rotational drive force of the threaded rotor 74 into linear drive force. The end mounts 86 and 88 support the rails and the motor, and a coupling arm 90 transfers the linear drive motion of the half-nut 80 to the syringe plunger 76.

Although other motors may be used, the stepper motor 30 described above is a bipolar electric motor having a step angle of 1.8°, a voltage range of 5.4 V–6 V to drive, and a torque of 10–15 oz-in. The use of such an external rotor in accordance with the invention achieves a compact design and allows the rotor to be used as a direct link in the drive mechanism of the pump. Due to the use of the external rotor, a pump that employs fewer moving parts, is of compact design, is lightweight and is simpler and more cost effective to manufacture results. Additionally, a motor in accordance with the invention results in less friction between the parts and less inertia because there are fewer parts to the motor, thus resulting in lower power requirements. Lower power requirements permit: the use of smaller and more lightweight batteries thus increasing the portability of the motor.

It will be apparent from the foregoing that, while particular forms of the invention have been illustrated and described, other modifications can be made without departing from the spirit and scope of the invention. Accordingly, it is not intended that the invention be limited, except as by the appended claims.

What is claimed is:

1. Apparatus for applying a force to a fluid container to cause fluid in the container to move from one position to another, comprising:
   an electric motor comprising a stator and a rotor, the rotor providing rotational motion and being located such that it rotates about the stator;
   a drive device positioned on the outer surface of the rotor and rotating with the rotor for providing a rotational drive force; and
   a follower disposed in contact with the drive device and mounted in relation thereto so as to translate the rotational drive force of the drive device into a linear drive force, the follower having a contact surface and the follower being located so as to apply the linear drive force against the fluid container with the contact surface to move the fluid.

2. The apparatus of claim 1 wherein:
   the drive device comprises a cam; and
   the follower Comprises a cam follower positioned around the cam for moving in a linear manner in response to the rotational drive force of the cam, the cam follower having the contact surface which presses against the fluid container to move the fluid.

3. The apparatus of claim 2 wherein:
   the fluid container comprises a flexible conduit;
   the drive device comprises a plurality of cams, each rotated by a predetermined angle from adjacent cams;
   the follower comprises a plurality of cam followers, each of which is placed around a respective cam and each of which translates the particular cam motion into linear motion, each cam follower including a contact surface for pressing against the flexible conduit; and
   wherein the predetermined angle between adjacent cams is selected so that the contact surfaces of the cam followers press against the flexible conduit in a sequential manner causing a peristaltic effect.

4. The apparatus of claim 3 wherein:
the outer surface of the rotor includes a plurality of keyways, each keyway spaced apart from the adjacent keyways by the predetermined angle; and
each cam comprises a key for insertion in a respective keyway of the rotor outer surface.

5. The apparatus of claim 3 wherein the cam followers and contact surfaces comprise peristaltic fingers which move against and away from the flexible tubing in accordance with the cam motion of the respective cam.

6. The apparatus of claim 1 wherein: the drive device comprises a threaded surface; and the follower comprises:
a nut mounted on the threads for translating the rotational drive force of the threads into linear drive force; and
a coupling arm from the nut to the fluid container to couple the linear drive force of the nut to the fluid container to force the fluid in the fluid container to move.

7. The apparatus of claim 6 wherein:
the fluid container is a syringe device having a barrel in which the fluid to be moved resides and a plunger for moving the fluid out of or into the syringe barrel in accordance with the movement of the plunger; and
the coupling arm is coupled to the plunger of the syringe to move the plunger in accordance with the rotational driving force of the drive device.

8. The apparatus of claim 7 wherein:
the electric motor comprises a rotor which is elongated;
the drive device comprises threads formed in the rotor;
the follower comprises a half-nut having threads which are engaged with the threads of the drive device for movement of the half-nut along the rotor;
the fluid container is a syringe device having a barrel in which the fluid to be moved resides and a plunger for moving the fluid out of or into the syringe barrel in accordance with the movement of the plunger; and
the coupling arm is coupled to the plunger of the syringe to move the plunger in accordance with the rotational driving force of the drive device.

9. Apparatus for applying a force to a fluid tubing to cause fluid in the tubing to move from one position to another, comprising:
an electric motor comprising a stator and a rotor, the rotor providing rotational motion and being located about the stator;
a cam positioned on the outer surface of the rotor and rotating with the rotor for providing a rotational driving force; and
a cam follower disposed in contact with the cam and mounted in relation thereto so as to translate the rotational drive force of the cam into a linear drive force, the cam follower having a contact surface and the follower being located so as to apply the linear drive force against the flexible tubing with the contact surface to move the fluid in accordance with the movement of the cam.

10. The apparatus of claim 9 further comprising:
a plurality of cams, each of which is mounted on the rotor and each of which is rotated by a predetermined angle from adjacent cams;
a plurality of cam followers, each of which is placed around a respective cam and each of which translates the respective cam motion into linear motion, each cam follower including a contact surface for pressing against the flexible conduit at a different location; and
wherein the predetermined angle between adjacent cams is selected so that the contact surfaces of the cam followers press against the flexible conduit in a sequential manner causing a peristaltic effect.

11. The apparatus of claim 10 wherein:
the outer surface of the rotor includes a plurality of keyways, each keyway spaced apart from the adjacent keyways by the predetermined angle; and
each cam comprises a key for insertion into a respective keyway of the rotor outer surface.

12. Apparatus for applying a force to a fluid container to cause fluid in the container to move from one position to another, comprising:
an electric motor comprising a stator and a rotor, the rotor providing rotational motion and being located about the stator;
wherein the rotor includes threads formed in its outer surface for providing a rotational driving force; and
a follower comprising a nut mounted on the threads of the rotor for translating the rotational drive force of the threads into linear drive force, the follower further comprising a coupling arm from the nut to the fluid container to couple the linear drive force of the nut to the fluid container to force the fluid in the fluid container to move the fluid.

13. The apparatus of claim 12 wherein:
the fluid container is a syringe device having a barrel in which the fluid to be moved resides and a plunger for moving the fluid out of or into the syringe barrel in accordance with the movement of the plunger; and
the coupling arm is coupled to the plunger of the syringe to move the plunger in accordance with the linear drive force of the nut.

14. The apparatus of claim 12 wherein:
the rotor is elongated;
the follower comprises a half-nut having threads which are engaged with the threads of the rotor for movement of the half-nut along the rotor;
the fluid container is a syringe device having a barrel in which the fluid to be moved resides and a plunger for moving the fluid out of or into the syringe barrel in accordance with the movement of the plunger; and
the coupling arm is coupled to the plunger of the syringe to move the plunger in accordance with the rotational driving force of the drive device.

15. A method for moving a fluid in a fluid container comprising the steps of:
positioning a rotor in relation to a stator such that a motor is formed in which the rotor rotates about the stator;
converting the rotational drive force of the rotor into linear drive force; and
applying the linear drive force to the fluid container to move the fluid.

16. The method of claim 15 wherein the step of converting the rotational drive force further comprises:

outputting the rotational drive force through a cam; and receiving the cam motion and translating the cam motion into linear motion.

17. The method of claim 15 wherein the step of converting the rotational drive force comprises:

outputting the drive force through a plurality of cams which are respectively positioned on the rotor such that they are rotated from adjacent cams by a predetermined angle; and converting the motions of the cams to respective linear drive motions and applying the linear drive motions to the container at different locations thereby resulting in a peristaltic effect.

18. The method of claim 15 wherein the step of converting the rotational drive force comprises:

converting the rotational drive force to helical drive motion through threads located on the external surface of the rotor; and converting the helical drive motion of the threads to linear drive motion through the use of a nut device confined to travel in only a linear motion and engaged with the threads.

* * * * *